United States Patent [19]

Gaccione

[11] 4,007,530
[45] Feb. 15, 1977

[54] QUICK-RELEASE DENTAL CLAMP

[76] Inventor: Carmine Gaccione, 4 John Jay Place, Rye, N.Y. 10580

[22] Filed: Sept. 16, 1975

[21] Appl. No.: 613,912

[52] U.S. Cl. .................................................. 32/36
[51] Int. Cl.² ........................................... A61C 5/12
[58] Field of Search ........................... 32/36, 35, 34

[56] References Cited
FOREIGN PATENTS OR APPLICATIONS
80,912  10/1952  Norway .................................. 32/36

Primary Examiner—Louis G. Mancene
Assistant Examiner—Jack Q. Lever

[57] ABSTRACT

A clamp usable by dentists to retain a rubber dam in a depressed position so as to isolate a tooth being worked on from mouth saliva and moisture. The clamp is constituted by a bow spring whose legs are joined to jaws adapted to grip the tooth, the spring being so biased as to normally spread the jaws apart. Associated with the legs of the spring is a trigger mechanism which, when the legs of the bow spring are pressed together to cause the jaws to grip the tooth, acts to lock the jaws in this position, and at the same time to cock the trigger, the mechanism including a trigger pin passing through a hole in the yoke of the bow springs. When this pin is actuated, the jaws are immediately spread apart by the released spring tension.

6 Claims, 4 Drawing Figures

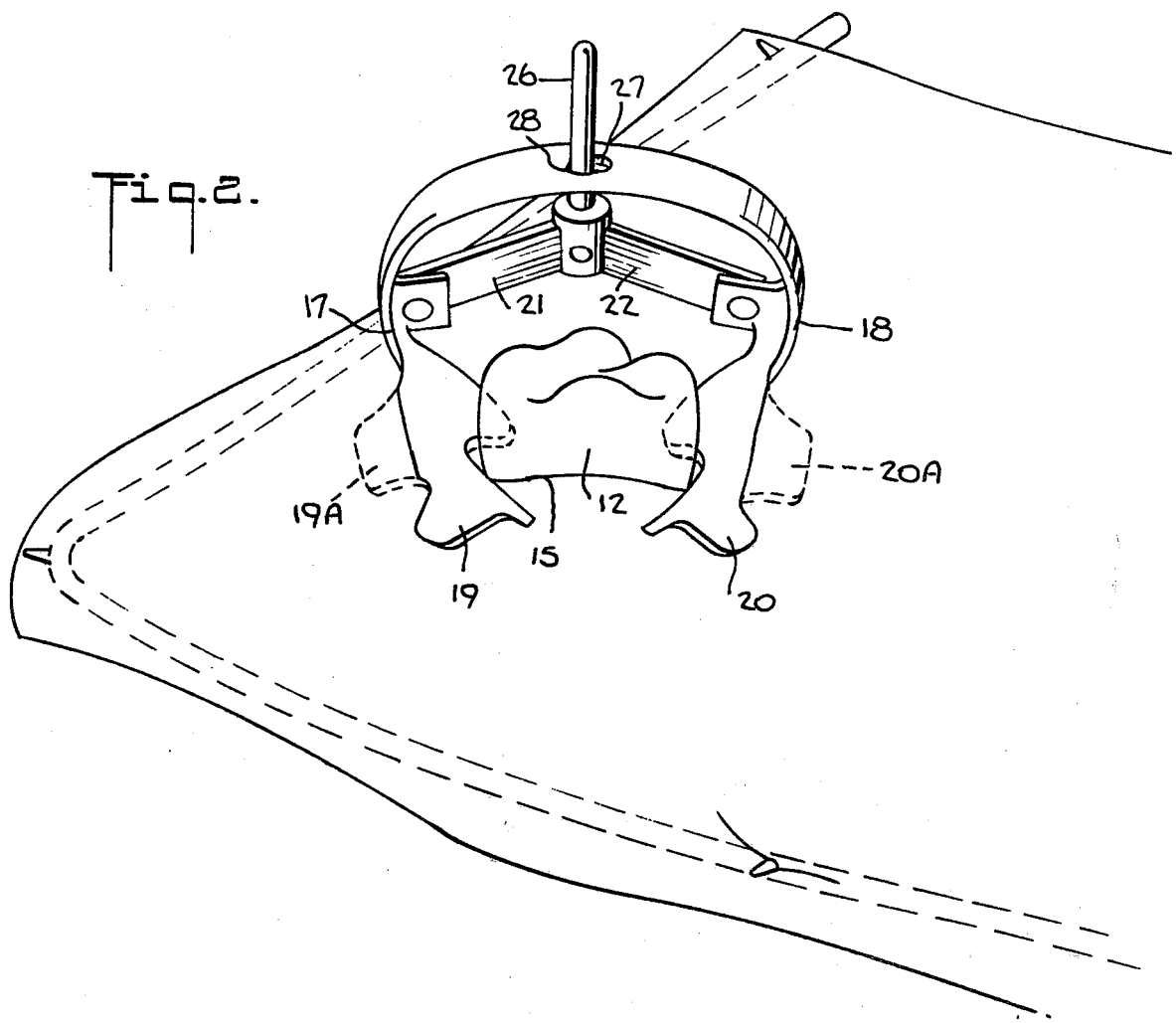
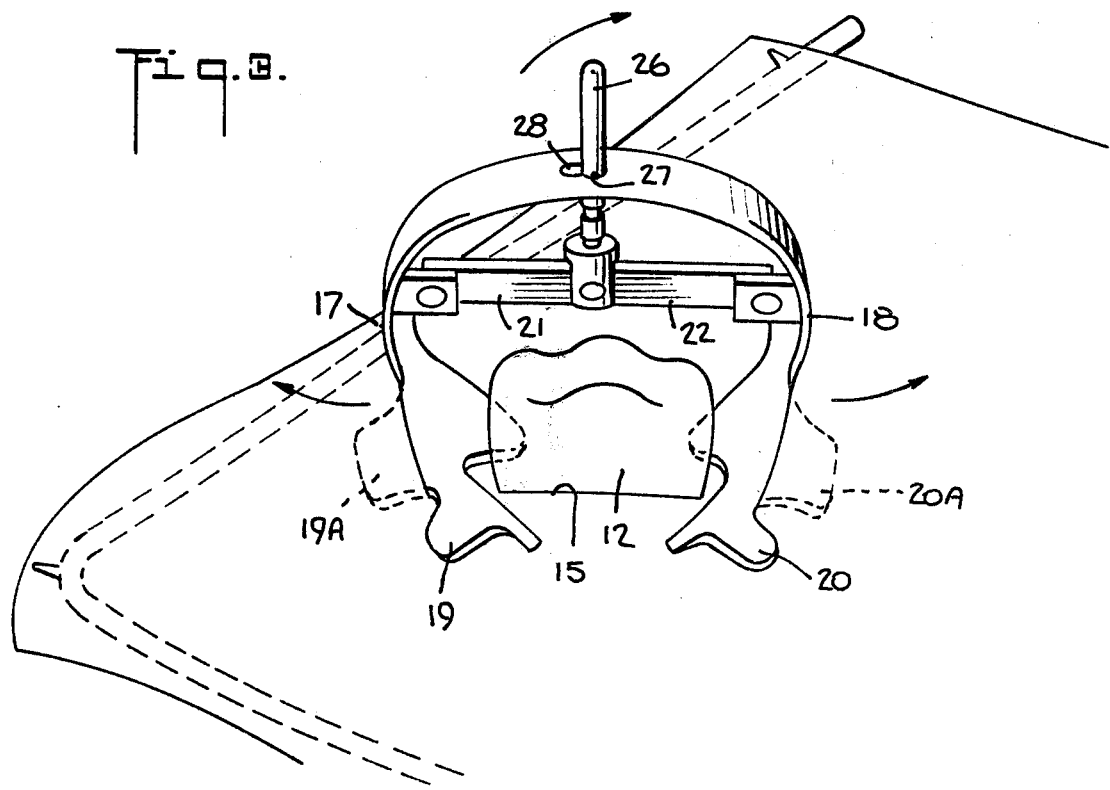

QUICK-RELEASE DENTAL CLAMP

BACKGROUND OF INVENTION

This invention relates generally to clamps usable by dentists to retain a rubber dam in a depressed position, and more particularly to a clamp which may be quickly released.

In certain operations, dentists find it necessary to isolate the tooth being worked on from mouth saliva and moisture. Usually this is accomplished by means of a dam in the form of a thin sheet of rubber having a small hole punched therein to accommodate the tooth being worked on. The dam is held by a clamp in a depressed position over the gum to expose the tooth at the work area. With the dam applied and held in position by the clamp, the dentist is then free to work on the tooth without fear of moisture or foreign matter interfering with or contaminating the operation.

Typical of rubber dam clamps in present use is the clamp disclosed in the Ivory U.S. Pat. No. 1,532,821. The Ivory clamp is constituted by a bow spring whose legs are joined to a pair of jaws shaped to engage a tooth, the bow spring being inwardly biased, whereby the jaws are normally closed. The jaws are provided with openings to receive forceps or a similar instrument, the outerside of the jaws having flanges extending laterally therefrom.

In using a clamp of the Ivory type, first the hole in the rubber dam is distended and the jaw flanges inserted therein. The forceps are then inserted in the openings of the jaws and the jaws of the clamp are spread apart, carrying with them the rubber dam mounted on the flanges. With the jaws spread apart, they may then be positioned over the tooth and when released from the forceps, the jaws grip the body of the tooth. Because of the pressure exerted by the bow spring, the clamp and rubber dam carried thereon are securely held in the desired position. Thereafter, to remove the clamp and dam from the tooth, the forceps are reinserted in the jaw openings and the jaws spread apart to disengage the body of the tooth.

It is sometimes necessary in emergency situations such as vomiting or with a management case in pedodontics, to immediately remove the dam to prevent any kind of trauma to the patient. When the dam is held in place by a clamp requiring a tool to effect disengagement, its immediate removal cannot be effected. Other clamp designs involve set screws to adjust the jaws about the tooth, and these, too, resist immediate removal of the clamp and dam. Should the dentist in an emergency situation therefore find it necessary forcibly to pull off the clamp, this action may cause injury to the patient.

SUMMARY OF INVENTION

In view of the foregoing, it is the main object of this invention to provide a clamp for retaining and securely holding a rubber dam in a depressed position to expose a tooth being worked on by a dentist while isolating the tooth from mouth saliva and moisture, the clamp being quickly releasable to prevent trauma to a patient in an emergency situation.

Among the significant features of a clamp in accordance with this invention, apart from the fact that it may be quickly released, are that the clamp causes neither discomfort nor pain to the patient, its design avoids damage to the tooth or gums, and when applied to the tooth the clamp is sufficiently removed from the field of work as not to obstruct the use of dental tools.

More particularly, it is an object of the invention to provide a dental clamp having jaws which grip the tooth of the patient, the jaws being immediately disengaged from the tooth by a simple trigger action.

Also an object of the invention is to provide an inexpensive and simple clamp having a trigger mechanism which operates efficiently and reliably.

Briefly stated, these objects are attained in a clamp usable with a rubber dam and constituted by a bow spring formed by a yoke and a pair of legs, the legs being joined to a pair of forwardly-projecting jaws contoured to engage the body of the tooth, the bow spring being so biased as to normally spread the jaws apart.

Associated with the bow spring is a trigger mechanism including a pair of links whose outer ends are pivoted to the legs and whose inner ends are hinged to a trigger head, whereby the links bridge the legs of the spring. Extending upwardly from the head is a trigger pin that passes through a center hole in the yoke. The center hole is formed with a lateral locking groove which, when the pin is displaced from its vertical axis, engages a notch on the pin to lock the jaws.

In the passive state of the clamp, with its jaws spread apart, the links are colinear. In order to activate the clamp, the legs are pressed inwardly against the tension of the bow spring, thereby causing the jaws to clamp onto a tooth and at the same time causing the links to assume a reverse-V formation, as a result of which the pin moves upwardly in the yoke hole. By then tilting the pin to one side into the locking groove, the activated clamp is retained in this state to hold the dam in place.

When it is necessary to release the clamp because of an emergency or for the routine removal of the dam, the trigger pin is shifted back into the yoke hole and the released bow spring immediately acts to spread the jaws apart, at which point the clamp again assumes its passive state.

OUTLINE OF DRAWINGS

For a better understanding of the invention as well as other objects and further features thereof, reference is made to the following detailed description to be read in conjunction with the accompanying drawings, wherein:

FIG. 2 shows the clamp in the activated state applied to a tooth;

FIG. 3 illustrates the clamp after its quick release; and

DESCRIPTION OF INVENTION

Figure 1:
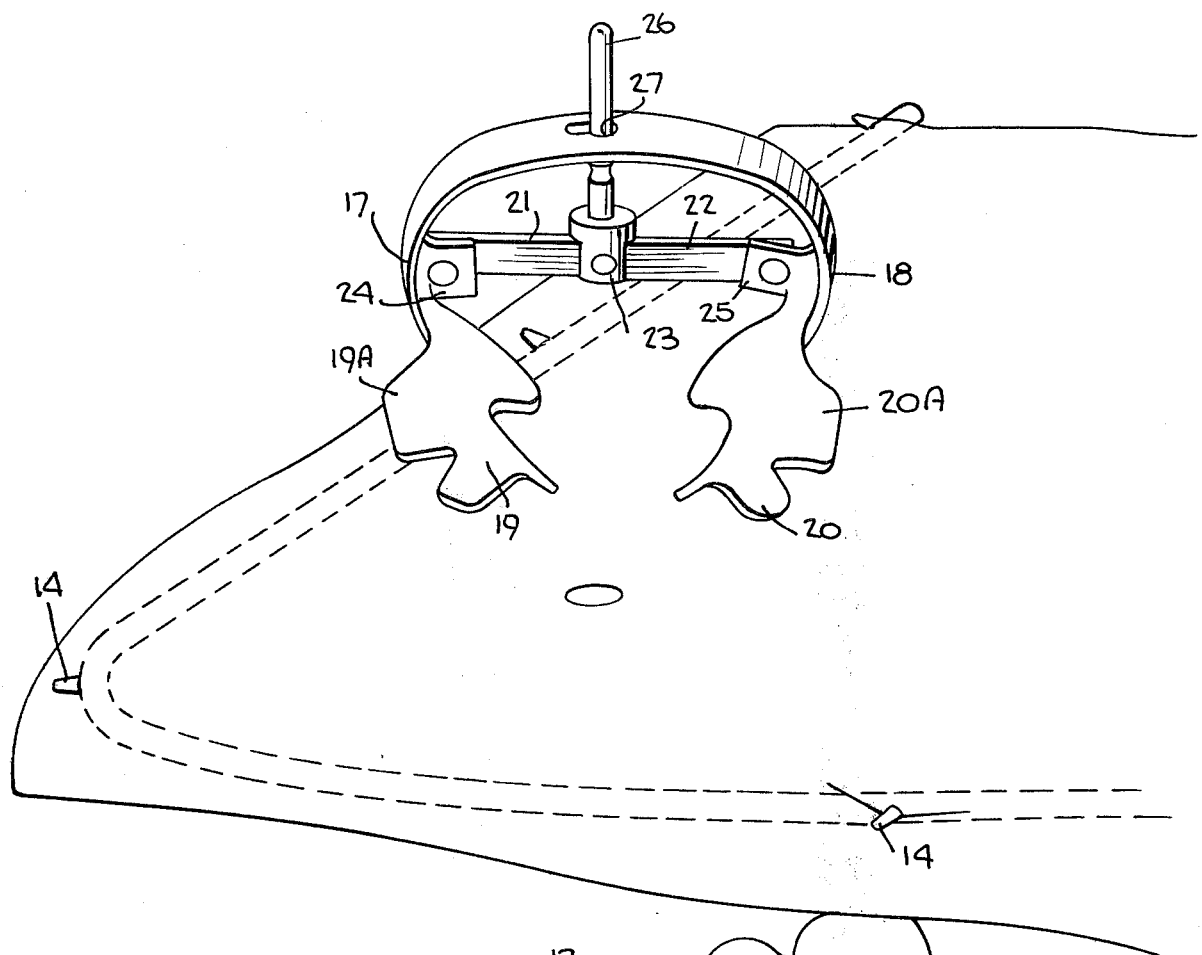
FIG. 1 is a perspective view of a preferred embodiment of a clamp in accordance with the invention in the passive state, the clamp being shown prior to its association with a rubber dam.

Referring now to FIG. 1, there is illustrated a clamp in accordance with the invention, the clamp being generally designated by reference numeral 10. The clamp is usable with a standard rubber dam 11 for the purpose of isolating from mouth saliva and moisture a tooth 12 to be worked on.

Dam 11 takes the form of a thin sheet of rubber which is supported in a smooth plane by means of a U-shaped metal frame 13 having points 14 thereon which pierce the margin of the stretched sheet to hold it across the frame. A small hole 15 is punched in dam 11 to accommodate tooth 12. When the rubber sheet is pressed down against the gum by the tooth-engaging clamp, the sheet is further stretched.

Clamp 10 is fabricated of a suitable spring metal such as stainless steel. The clamp includes a bow-spring constituted by an arched-shape yoke 15 having a pair of legs 17 and 18 depending therefrom. Legs 17 and 18 are joined to forwardly projecting jaws 19 and 20 whose inner edges are profiled to conform generally to the contours of a tooth. The outer edges of jaws 19 and 20 have flanges 19A and 20A extending laterally therefrom, the flanges being concave to conform to the gum line.

Clamp 10 is provided with a trigger mechanism formed by a pair of identical links 21 and 22 in slat form which together bridge the bow-spring legs 17 and 18. The inner ends of the links are hinged to a trigger head 23, while the outer ends thereof are pivotally connected to legs 17 and 18 by lugs 24 and 25.

Figure 4:
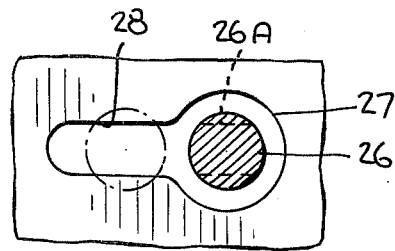
FIG. 4 shows the relationship between the trigger pin of the clamp and a latching hole.

Anchored in trigger head 23 and extending upwardly therefrom is a trigger pin 26 which passes through a circular hole 27 in the center of yoke 16. The diameter of hole 27 is greater than that of pin 26, so that the pin is loose therein. As best seen in FIG. 4, extending laterally from hole 27 is an oblong bay 28 which is narrower than the diameter of pin 26 but which can accommodate a notch 26A formed in the pin, so that the bay acts to latch the pin.

In the passive state of the clamp, which is the state shown in FIG. 1, the normal bias of the bow spring is such as to hold jaws 19 and 20 apart. In this state, links 21 and 22 coupled to legs 17 and 18 of the spring are in co-linear relationship, and trigger pin 26 is received loosely in hole 27.

In operation, hole 15 in rubber dam 11 is distended, as shown in FIG. 2, so that jaw flanges 19A and 20A may be inserted into the hole to lie under the dam, and the clamp and dam assembly is then brought down over tooth 12 which projects through distended hole 15. Legs 17 and 18 are then pressed inwardly against the tension of the bow spring to cause the jaws of the clamp to grip the tooth.

In pressing the legs inwardly, links 21 and 22 assume an inverted V-formation and trigger pin 26 rides upwardly in yoke hole 27 until the latching notch 26A in the pin which is adjacent its lower end is in registration with bay 28, at which point the pin is tilted toward bay 28 to lock the trigger mechanism. This is the activated state of the clamp, for now the jaws of the clamp securely grip the tooth being worked on and the trigger mechanism is cocked in readiness for fixing to immediately release the clamp.

When it becomes necessary in an emergency or for normal purposes to remove the clamp from the tooth, the dentist merely switches the trigger pin out of bay 28 into its midline position in yoke hole 27. As a result of this action, the bow spring legs are released and expand to resume their normal position, thereby retracting jaws 19 and 20 from the tooth, as shown in FIG. 3. Because the rubber dam, when the clamp is in its activated mode, is pressed down against the gum and is thereby stretched, when the trigger mechanism is fixed and the clamp jaws are withdrawn, the dam is also released. The released dam resumes its planar form on frame 13, as a result of which it acts to pop the clamp off the tooth.

Thus no tool is necessary to lock the clamp to the tooth (other than the usual clamp holder to place the clamp on the tooth) or to remove it therefrom, and it is possible, when the occasion arises, by simply firing the trigger mechanism to immediately release the clamp and the dam carried thereby.

While there has been shown and described a preferred embodiment of a quick release clamp mechanism in accordance with the invention, it will be appreciated that many changes and modifications may be made therein without, however, departing from the essential spirit thereof. Thus, instead of latching the trigger pin by means of a latching groove, the pin may be provided with a depressible detent, which, when the pin is pushed upwardly in the center hole, goes through the hole and then projects outwardly from the pin to lock it. To release the pin, one then merely presses in the detent button.

I claim:

1. A clamp usable with a rubber dam for engaging a tooth to permit a dentist to work thereon without interference from mouth saliva and moisture, said clamp comprising:
   A. a bow spring having a yoke and a pair of legs depending therefrom, said yoke being provided with a center hole;
   B. a pair of jaws joined to the ends of said legs and extending forwardly therefrom the inner edge of said jaws being contoured to engage said tooth, said bow spring having a normal bias maintaining said jaws in a spread-apart passive state; and
   C. a trigger mechanism constituted by a pair of links hinged to a trigger head, the ends of said links being pivoted to said legs whereby in said passive state said links bridge said legs to assume a colinear relationship, a trigger pin anchored in said head and extending upwardly through said yoke hole, whereby when said legs are pressed inwardly against the tension of the spring to cause said clamp to assume an activated state, the pin rides up the hole and the jaws are caused to engage said tooth, and releasable means to hold said pin to maintain said activated state, which means, when actuated, frees said pin, whereby when said releasable means are actuated to fire said trigger mechanism, said pin rides down the hole and the jaws are immediately retracted from the tooth.

2. A clamp as set forth in claim 1, wherein said jaws are provided at their outer edges with flanges to enter a hole in said dam.

3. A clamp as set forth in claim 1, wherein said releasable means is constituted by a bay extending laterally from said hole and a groove in said pin, whereby said groove enters said bay when said pin is tilted.

4. A clamp as set forth in claim 1, wherein said releasable means is a depressible detent in said pin.

5. A clamp as set forth in claim 1, wherein said links are pivoted to said legs by means of lugs attached to the legs.

6. A clamp as set forth in claim 1, wherein said links are in slat form.

* * * * *